United States Patent [19]

Limon

[11] Patent Number: 5,476,505
[45] Date of Patent: Dec. 19, 1995

[54] COILED STENT AND DELIVERY SYSTEM

[75] Inventor: Timothy A. Limon, Cupertino, Calif.

[73] Assignee: Advanced Cardiovascular Systems, Inc., Santa Clara, Calif.

[21] Appl. No.: 154,266

[22] Filed: Nov. 18, 1993

[51] Int. Cl.$^6$ ........................................ A61F 2/06
[52] U.S. Cl. ........................ 623/1; 623/12; 606/191; 606/198; 604/109
[58] Field of Search .................. 623/1, 11, 12; 604/106, 109; 606/191, 198

[56] References Cited

U.S. PATENT DOCUMENTS

| | | |
|---|---|---|
| 3,105,492 | 10/1963 | Jeckel . |
| 3,868,956 | 3/1975 | Alfidi et al. . |
| 4,130,904 | 12/1978 | Whalen . |
| 4,300,244 | 11/1981 | Bokros . |
| 4,503,569 | 3/1985 | Dotter . |
| 4,512,338 | 4/1985 | Balko et al. . |
| 4,531,933 | 7/1985 | Norton et al. . |
| 4,553,545 | 11/1985 | Maass et al. . |
| 4,580,568 | 4/1986 | Gianturco . |
| 4,585,000 | 4/1986 | Hershenson . |
| 4,649,922 | 3/1987 | Wiktor . |
| 4,655,771 | 4/1987 | Wallsten . |
| 4,681,110 | 7/1987 | Wiktor . |
| 4,706,671 | 11/1987 | Weinrib . |
| 4,760,849 | 8/1988 | Kropf . |
| 4,762,128 | 8/1988 | Rosenbluth . |
| 4,773,432 | 9/1988 | Rydell . |
| 4,795,458 | 1/1989 | Regan . |
| 4,800,882 | 1/1989 | Gianturco . |
| 4,820,298 | 4/1989 | Leveen et al. . |
| 4,830,003 | 5/1989 | Wolff et al. . |
| 4,848,342 | 7/1989 | Kaltenbach ........................ 606/198 |
| 4,878,906 | 11/1989 | Lindemann et al. . |
| 4,907,336 | 3/1990 | Gianturco . |
| 4,969,458 | 11/1990 | Wiktor . |
| 4,969,890 | 11/1990 | Sugita et al. . |
| 4,990,151 | 2/1991 | Wallsten . |
| 4,990,156 | 2/1991 | Lefebvre . |
| 4,998,539 | 3/1991 | Delsanti . |
| 5,002,560 | 3/1991 | Machold et al. . |
| 5,019,090 | 5/1991 | Pinchuk . |
| 5,026,377 | 6/1991 | Burton et al. . |
| 5,034,001 | 7/1991 | Garrison et al. . |
| 5,037,427 | 8/1991 | Harada et al. . |
| 5,041,126 | 8/1991 | Gianturco . |
| 5,059,211 | 10/1991 | Stack et al. ........................ 623/1 |
| 5,062,829 | 11/1991 | Pryor et al. . |
| 5,064,435 | 11/1991 | Porter . |
| 5,071,407 | 12/1991 | Termin et al. . |
| 5,089,005 | 2/1992 | Harada . |
| 5,092,877 | 3/1992 | Pinchuk . |
| 5,108,417 | 4/1992 | Sawyer . |
| 5,135,517 | 8/1992 | McCoy . |
| 5,163,952 | 11/1992 | Froix . |
| 5,163,958 | 11/1992 | Pinchuk . |
| 5,180,368 | 1/1993 | Garrison . |
| 5,183,085 | 2/1993 | Timmermans . |
| 5,192,297 | 3/1993 | Hull . |
| 5,197,978 | 3/1993 | Hess . |
| 5,222,969 | 6/1993 | Gillis . |
| 5,226,913 | 7/1993 | Pinchuk . |
| 5,234,456 | 8/1993 | Silvestrini . |
| 5,242,451 | 9/1993 | Harada et al. . |
| 5,256,146 | 10/1993 | Ensminger et al. . |
| 5,258,020 | 11/1993 | Froix . |
| 5,263,964 | 11/1993 | Purdy . |

*Primary Examiner*—Paul B. Prebilic
*Attorney, Agent, or Firm*—Fulwider Patton Lee & Utecht

[57] ABSTRACT

An intravascular stent and delivery system comprising a helically-shaped spring and means for expanding the stent from a first diameter to a second larger diameter, and releasing the stent for implantation within a vessel lumen; a method for intraluminal implantation of an intravascular stent using the said device. The stent and delivery device are particularly adapted to hold open a blood vessel after a vascular procedure therein such as an angioplasty.

7 Claims, 1 Drawing Sheet

COILED STENT AND DELIVERY SYSTEM

BACKGROUND OF THE INVENTION

This invention generally relates to intraluminal stents and vascular catheters suitable for maintaining the patency of a blood vessel after a vascular procedure therein, such as angioplasty.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guidewire and a dilatation catheter having an inflatable balloon on the distal end thereof are introduced through the guiding catheter with the guidewire slidably disposed within an inner lumen of the dilatation catheter. The guidewire is first advanced out of the distal end of the guiding catheter and is maneuvered into the patient's coronary vasculature containing the lesion to be dilated, and is then advanced beyond the lesion. Thereafter, the dilatation catheter is advanced over the guidewire until the dilatation balloon is located across the lesion. Once in position across the lesion, the balloon of the dilatation catheter is filled with radiopaque liquid at relatively high pressures (e.g., greater than about 4 atmospheres) and is inflated to a predetermined size (preferably the same as the inner diameter of the artery at that location) to radially compress the atherosclerotic plaque of the lesion against the inside of the artery wall to thereby dilate the lumen of the artery. The balloon is then deflated so that the dilatation catheter can be removed and blood flow resumed through the dilated artery.

By way of example, further details of angioplasty procedures and the devices used in such procedures can be found in U.S. Pat. No. 4,323,071 (Simpson, et al.), U.S. Pat. No. 4,332,254 (Lundquist), U.S. Pat. No. 4,439,185 (Lundquist), U.S. Pat. No. 4,168,224 (Enzmann, et al.), U.S. Pat. No. 4,516,972 (Samson), U.S. Pat. No. 4,582,181 (Samson), U.S. Pat. No. 4,538,622 (Samson, et al.), U.S. Pat. No. 4,597,755 (Samson), U.S. Pat. No. 4,616,652 (Simpson), U.S. Pat. No. 4,748,982 (Horzewski, et al.), U.S. Pat. No. 4,771,778 (Mar), and U.S. Pat. No. 4,793,350 (Mar, et al.) which are hereby incorporated herein in their entirety.

A common problem that sometimes occurs after an angioplasty procedure is the appearance of restenosis at or near the site of the original stenosis in the blood vessel which requires a secondary angioplasty procedure or a bypass surgery. Another occurrence which reduces the success of an angioplasty procedure is that frequently the stenotic plaque or intima of the blood vessel or both are dissected during the angioplasty procedure by the inflation of the balloon. Upon the deflation of the balloon, a section of the dissected lining (commonly termed "flap") will collapse into the bloodstream, thereby closing or significantly reducing the blood flow through the vessel. In these instances, emergency bypass surgery is sometimes required to avoid a myocardial infarct distal to the blockage.

Conceivably, the dilatation catheter could be replaced with a perfusion type dilatation catheter such as described in U.S. Pat. No. 4,790,315 in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In recent years, various devices and methods (other than bypass surgery) for prevention of restenosis and repairing damaged blood vessels have become known which typically use an expandable cage or region (commonly termed "stent") on the distal end of the catheter designed to hold a detached lining against an arterial wall for extended periods to facilitate the reattachment thereof. Some stents are designed for permanent implantation inside the blood vessel and others are designed for temporary use inside the vessel. By way of example, several stent devices and methods can be found in U.S. Pat. No. 4,998,539, U.S. Pat. No. 5,002,560, U.S. Pat. No. 5,034,001 (Garrison, et al.), U.S. Pat. No. 5,133,732 (Wiktor), and U.S. Pat. No. 5,180,368 (Garrison).

Typically, the expandable region of these stents is formed by a braided wire attached to the distal end of the catheter body. Such braided designs are difficult and expensive to manufacture, and can create reliability concerns due to the existence of high stress points located at the connection of the braided wire region with the catheter body and at the connections between the intermingled wire strands.

Alternatively, the expandable stent can be formed by a helical metal or plastic spring that is mechanically restrained in a contracted state during delivery to a predetermined position within a vessel. After placement, the mechanical restraint is released, allowing the helical spring stent to expand rapidly against the inner walls of the vessel. Examples of such stents are disclosed in U.S. Pat. No. 4,768,507 (Fischell, et al.), U.S. Pat. No. 4,990,155 (Wilkoff), and U.S. Pat. No. 4,553,545 (Maass, et al.). Each of these patents discloses a method for percutaneous transluminal insertion of a coiled stent that is mechanically restrained until released. Each system requires axial displacement of the delivery system to release the coiled stent and to disengage the stent from the catheter. The disadvantage of the axial displacement is the possibility that the additional intravascular manipulation and translation required to disengage the coiled stent from the delivery device may lead to undesirable damage to the vessel walls.

What has been needed and heretofore unavailable is an easily advanceable and removable low-profile intravascular catheter which can simply deliver a coiled stent to hold a collapsed dissected lining or flap against the blood vessel wall for sufficient time to allow the natural adhesion of the flap to the blood vessel wall and to aid in the prevention of restenosis while simultaneously allowing for the perfusion of blood to locations distal to the stent without blocking a branch vessel. The present invention fulfills this need.

SUMMARY OF THE INVENTION

This invention is directed to a system for delivering a coiled stent which can hold a blood vessel open for a period of time after a vascular procedure therein and which allows for the perfusion of blood through the blood vessel while the blood vessel is held open.

The coiled stent and delivery system in accordance with the present invention includes a coiled stent formed from a helical spring designed to repair a vascular flap or other damage by compressing and holding the flap against the vessel wall until reattachment takes place.

The delivery system includes a catheter formed from coaxially arranged inner and outer flexible shafts, the distal ends of which have slots or apertures to engage the ends of the coiled stent.

The coiled stent is loaded onto the delivery catheter by engaging the proximal end of the stent with the aperture in the distal end of the outer flexible shaft, and by engaging the distal end of the coiled stent with the aperture in the distal end of the inner flexible shaft. The proximal ends of the flexible shafts are counter-rotated relative to each other to increase the tension on the coiled stent, thereby reducing its external diameter. When the coiled stent is loaded, the proximal ends of the inner and outer flexible shafts are locked in position relative to each other.

Upon placement at the site to be repaired, the proximal ends of the inner and outer flexible shafts are released and counter-rotated to reduce the tension on the coiled stent. Expansion of the coiled stent against the vessel wall results in an enlarged diameter of the coiled stent, with disengagement of the ends of the stent from the apertures in the distal ends of the inner and outer flexible shafts. No additional manipulation or axial displacement of the flexible shafts relative to each other is required to disengage the stent.

In a presently preferred embodiment, the coiled stent is formed from stainless steel, nickel-titanium alloy, plastic or a resorbable material. The flexible shafts are of tubular construction formed from plastic or other material capable of delivering torque. Torque is applied to the proximal ends of the inner shaft and outer shaft by means of knobs formed of plastic or other suitable material associated therewith.

The coiled stent and delivery system of the invention allows for the rapid advancement thereof over a guidewire or other guiding member to a vascular location wherein an occlusion has occurred. The coiled stent when expanded will hold the blood vessel open and simultaneously allow blood flow through the expandable region thereby eliminating or preventing ischemic conditions distal to the occlusion. These and other advantages of the invention will become more apparent from the following detailed description thereof when taken in conjunction with the accompanying exemplary drawings.

DETAILED DESCRIPTION OF THE INVENTION

Figure 1:
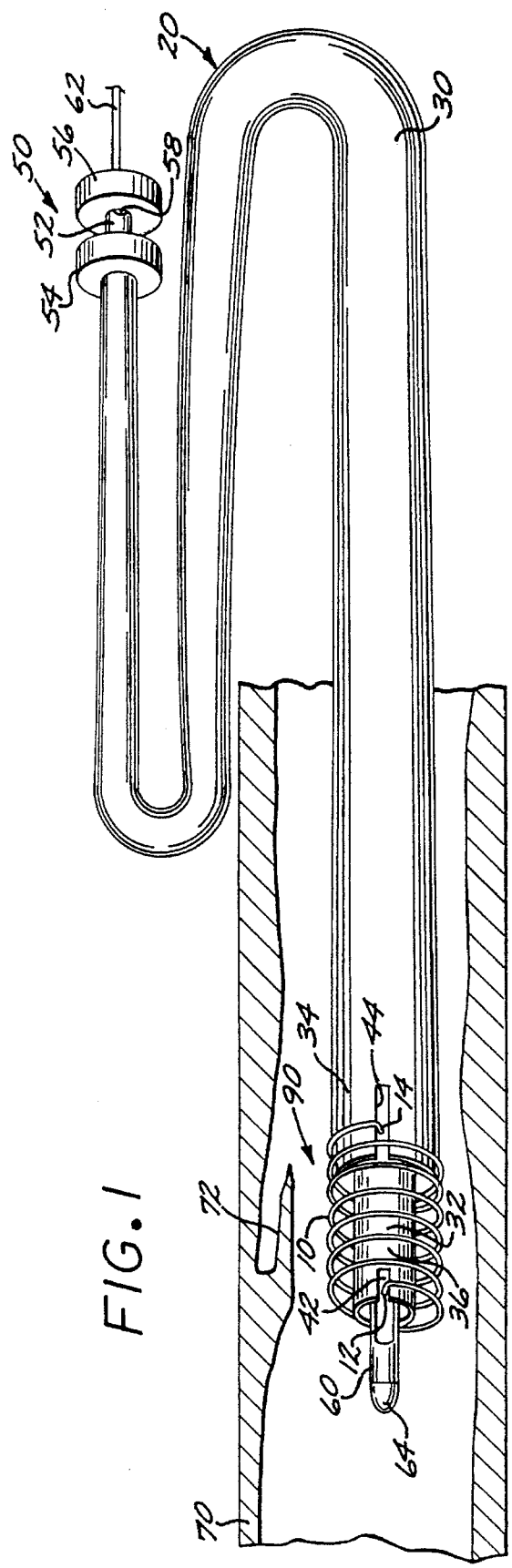
FIG. 1 is a plan view of the present invention, depicting the coiled stent in a contracted position loaded onto the delivery catheter.

FIG. 1 illustrates coiled stent 10 and delivery system assembly 20 embodying features of the invention. Coiled stent 10 has distal end 12 and proximal end 14, both of which are inwardly directed toward the longitudinal centerline. The delivery system assembly 20 generally includes an elongated catheter body 30, a stent transport region 90 and a control region 50.

The elongated tubular member which forms catheter body 30 has an inner flexible shaft 32 and an outer flexible shaft 34 that are coaxially arranged. Inner flexible shaft 32 resides within outer flexible shaft 34 and the shafts are free to rotate relative to each other.

The stent transport region 90 of delivery system assembly 20 comprises the distal end of elongated catheter body 30. The distal end of inner flexible shaft 32 has an aperture, here shown as longitudinal slot 42, in which is mounted distal end 12 of stent 10. The distal end of outer flexible shaft 34 has an aperture, here shown as longitudinal slot 44, in which is mounted proximal end 14 of stent 10. While the apertures in FIG. 1 are depicted as slots, the apertures could also be formed as holes or, more generally, as any type of opening in the wall of the inner and outer flexible shafts.

The control region 50 comprises the proximal end of delivery system assembly 20. The proximal ends of inner flexible shaft 32 and outer flexible shaft 34 are formed in a manner that allows inner flexible shaft 32 and outer flexible shaft 34 to be held and rotated relative to each other to increase or decrease torque that is transmitted through inner flexible shaft 32 and outer flexible shaft 34 resulting in an increase or decrease of tension in stent 10. By increasing and decreasing the tension in coiled stent 10, the radial dimension of stent 10 increases and decreases.

A locking device 52 provides a means for locking knobs 54 and 56 in position relative to each other. In the present embodiment, knob 54 is attached to outer flexible shaft 34, and knob 56 is attached to inner flexible shaft 32. For example, knobs 54 and 56 may be formed together with flexible shafts 32 and 34 from the same material, forming a single continuous piece; alternatively, knobs 54 and 56 may be formed from the same or a different material than flexible shafts 32 and 34, and attached to the proximal ends of flexible shafts 32 and 34 using a suitable means of attachment that ensures that torque applied to knobs 54 and 56 is transmitted to flexible shafts 32 and 34. Alternatively, the proximal ends of flexible shafts 32 and 34 can be formed in such a manner that knurls, ridges, or other devices are formed on the shaft surface that enable the secure gripping of the proximal ends of the shafts.

In the operation of delivery system assembly 20, coiled stent 10 is mounted onto the distal end of catheter body 30. The proximal end 14 of stent 10 is guided into slot 44 of outer flexible shaft 34. The distal end 12 of stent 10 is guided into slot 42 of inner flexible shaft 32. Knob 54 and knob 56 are rotated in a counter direction relative to each other to apply torque to inner flexible shaft 32 and outer flexible shaft 34, resulting in increased tension on coiled stent 10, reducing its diameter. The position of shafts 32 and 34 relative to each other is maintained by locking device 52. The distal end of delivery system assembly 20 is mounted on proximal end 62 of a guiding member 60 such as a guidewire which has been positioned across the area of vessel 70 containing flap 72 that requires repair. The proximal end of the guiding member is advanced through central passageway 36 of inner flexible shaft 32, and out of port 58. The proximal portion 62 of guiding member 60 is then manually held while delivery system assembly 20 is advanced over the guiding member to a defined location within the patient's blood vessel. Locking device 52 is released and knobs 54 and 56 are then counter-rotated relative to each other to reduce the tension of coiled stent 10. As tension is reduced, coiled stent 10 expands. As stent 10 expands, it presses against flap 72, pushing it against vessel wall 70, thus maintaining the patency of the vessel. When stent 10 expands against the vessel wall, and all tension on the stent has been released, stent ends 12 and 14 are either completely released from slots 42 and 44, or are loosely held within the slots. Delivery system assembly 20 is advanced toward proximal end 62 of guiding member 60 to remove it from the repair site in the vessel. Even if the expansion of stent 10 is not sufficient to free stent ends 12 and 14 from slots 42 and 44, delivery system assembly 20 may be removed without axial displacement of the distal ends of inner flexible shaft 32 and outer flexible shaft 34 relative to each other.

Figure 2:
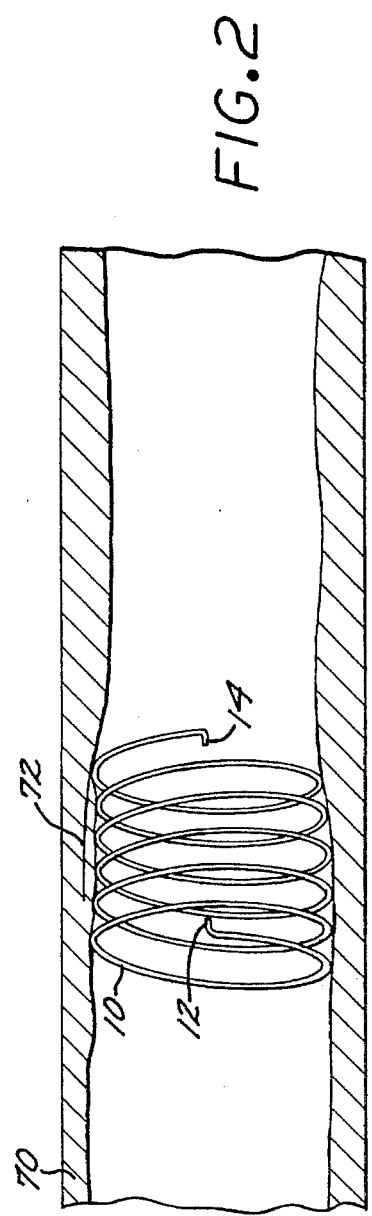
FIG. 2 is a plan view of the coiled stent in an expanded state depicted within a transverse cross-sectional view of a blood vessel.

FIG. 2 illustrates the positioning of coiled stent 10 in an expanded state pressing against flap 72 on vessel wall 70. This pressure is maintained permanently, allowing the flap to reattach to the vessel wall, while allowing blood to flow readily through the vessel.

While a particular form of the invention has been illustrated and described herein by way of example, it will be apparent that various modifications can be made without departing from the spirit and scope of the invention.

What is claimed is:

1. An intravascular stent and delivery system for intraluminal implantation in a patient's vasculature, comprising:

an intravascular stent formed of a helically-shaped spring having a first diameter and a second larger diameter, said stent further having an inwardly directed distal end and an inwardly directed proximal end; and a delivery device comprising:

a catheter having an outer flexible shaft surrounding and coaxially aligned with an inner flexible shaft, said inner flexible shaft having an inner lumen extending from a proximal guidewire port to a distal guidewire port for receiving a guidewire therein, said outer flexible shaft further having a distal end and a proximal end, said inner flexible shaft further having a distal end and a proximal end;

a first slot extending from said distal end of said inner flexible shaft and extending proximally for a distance for receiving said inwardly directed distal end of said stent;

a second slot extending from said distal end of said outer flexible shaft and extending proximally for a distance for receiving said inwardly directed proximal end of said stent;

means for rotating said inner flexible shaft relative to said outer flexible shaft to increase or decrease the tension on said stent and expand said stent from said first diameter to said second larger diameter;

a locking device positioned proximate said rotating means for locking said inner flexible shaft and said outer flexible shaft in position relative to each other; and means for releasing said distal end and said proximal end of said stent from said first slot and said second slot respectively without relative axial displacement between said stent and said delivery device.

2. The stent and delivery system of claim 1, wherein said stent is made from a flexible material having an elastic memory.

3. The stent and delivery system of claim 1, wherein said stent is made from stainless steel.

4. The stent and delivery system of claim 1, wherein said stent is made from nickel-titanium alloy.

5. The stent and delivery system of claim 1, wherein said stent is made from a resorbable material.

6. The stent and delivery system of claim 1, wherein said inner flexible shaft and outer flexible shaft are formed from plastic.

7. The stent and delivery system of claim 1, wherein the proximal end of said inner flexible shaft and said outer flexible shaft each have a knob associated therewith that facilitates rotating said inner flexible shaft and said outer flexible shaft relative to each other.

* * * * *